United States Patent [19]
Rogachevsky

[11] Patent Number: 5,752,927
[45] Date of Patent: May 19, 1998

[54] INFLATABLE CERVICAL TRACTION DEVICE

[76] Inventor: Richard J. Rogachevsky, P.O. Box 11652, Honolulu, Hi. 96828

[21] Appl. No.: 777,030

[22] Filed: Dec. 30, 1996

Related U.S. Application Data

[60] Provisional application No. 60/009,458 Dec. 29, 1995.

[51] Int. Cl.[6] ............................................. A61F 5/00
[52] U.S. Cl. ............................................. 602/18; 602/13
[58] Field of Search .............................. 602/13, 17, 18, 602/32, 36; 128/845, DIG. 20, DIG. 23; 601/11, 39, 148–152

[56] References Cited

U.S. PATENT DOCUMENTS

| | | | |
|---|---|---|---|
| 731,314 | 6/1903 | Malmqvist | 128/DIG. 23 X |
| 2,806,471 | 9/1957 | Breese | 128/DIG. 23 X |
| 3,164,151 | 1/1965 | Nicoll . | |
| 3,285,244 | 11/1966 | Cottrell | 128/DIG. 23 X |
| 3,343,532 | 9/1967 | Zumaglini | 602/18 |
| 3,610,235 | 10/1971 | Vagacs | 602/13 |
| 3,765,412 | 10/1973 | Ommaya . | |
| 4,372,297 | 2/1983 | Perlin | 128/DIG. 20 X |
| 4,407,274 | 10/1983 | Goodley . | |
| 4,583,522 | 4/1986 | Aronne | 601/149 X |
| 4,597,384 | 7/1986 | Whitney | 128/DIG. 20 X |
| 4,890,605 | 1/1990 | Rosendale . | |
| 4,922,893 | 5/1990 | Wright et al. | 601/152 |
| 4,971,043 | 11/1990 | Jones . | |
| 5,047,287 | 9/1991 | Horiuchi et al. . | |
| 5,060,661 | 10/1991 | Howard | 602/18 X |
| 5,067,483 | 11/1991 | Freed . | |
| 5,109,835 | 5/1992 | McDonald et al. . | |
| 5,297,539 | 3/1994 | Liebl et al. . | |
| 5,308,359 | 5/1994 | Lossing . | |
| 5,382,226 | 1/1995 | Graham . | |
| 5,402,535 | 4/1995 | Green | 128/DIG. 23 X |
| 5,403,266 | 4/1995 | Bragg et al. . | |
| 5,454,781 | 10/1995 | Chitwood . | |

*Primary Examiner*—Linda C. Dvorak
*Attorney, Agent, or Firm*—Michael I. Kroll

[57] ABSTRACT

An inflatable cervical traction device (10) comprising a C-shaped multi-ribbed inflatable hollow collar (12) having four separate chambers (14), (16), (18) and (20). Two of the chambers (14) and (16) are located at rear right and left locations of the collar (12), while the other two chambers (18) and (20) are located at front right and left locations of the collar (12). Structures (22) are for securing two opposite front ends of the collar (12) together in a releasable manner, to hold the collar (12) about a neck (24) of a person (26). A facility (28) is for pumping air into the four chambers (14), (16), (18) and (20) of the collar (22) to inflate each of the four chambers (14), (16), (18) and (20) at various pressurized amounts, so that the collar (12) can properly support the neck (24) of the person (26). An assembly (30) is for releasing air from the four chambers (14), (16), (18) and (20) of the collar (12), so that the collar (12) can deflate to be easily removed from the neck (24) of the person (26).

21 Claims, 11 Drawing Sheets

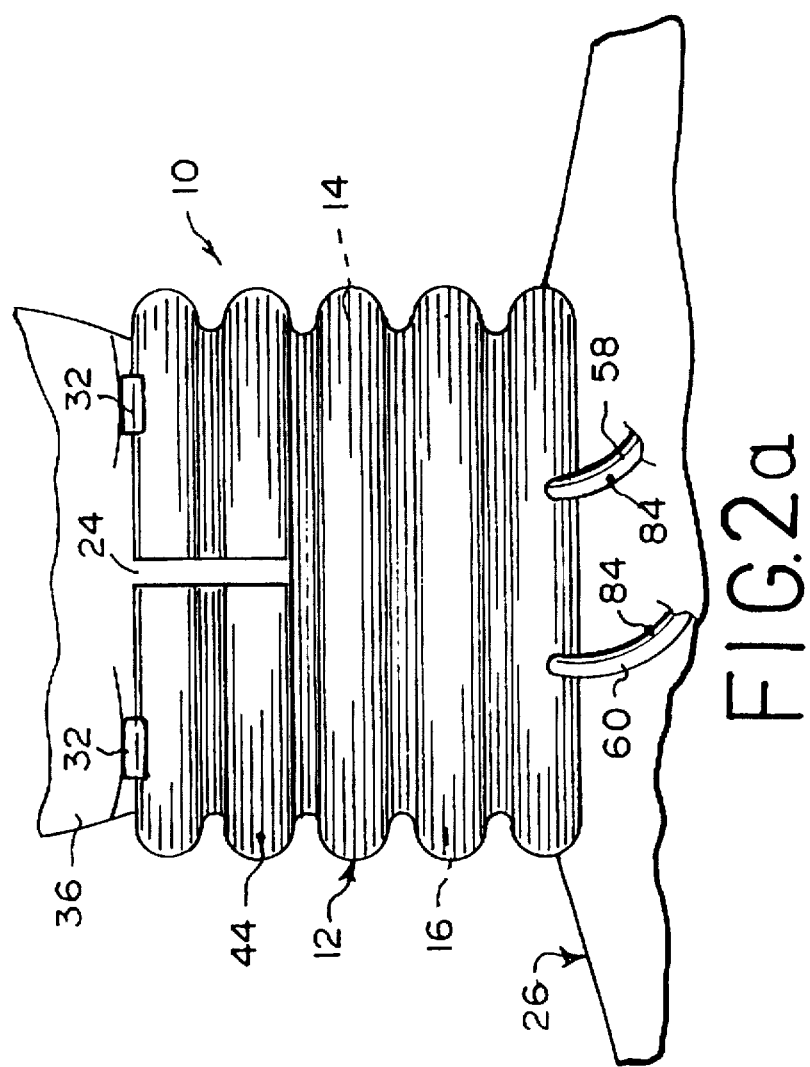

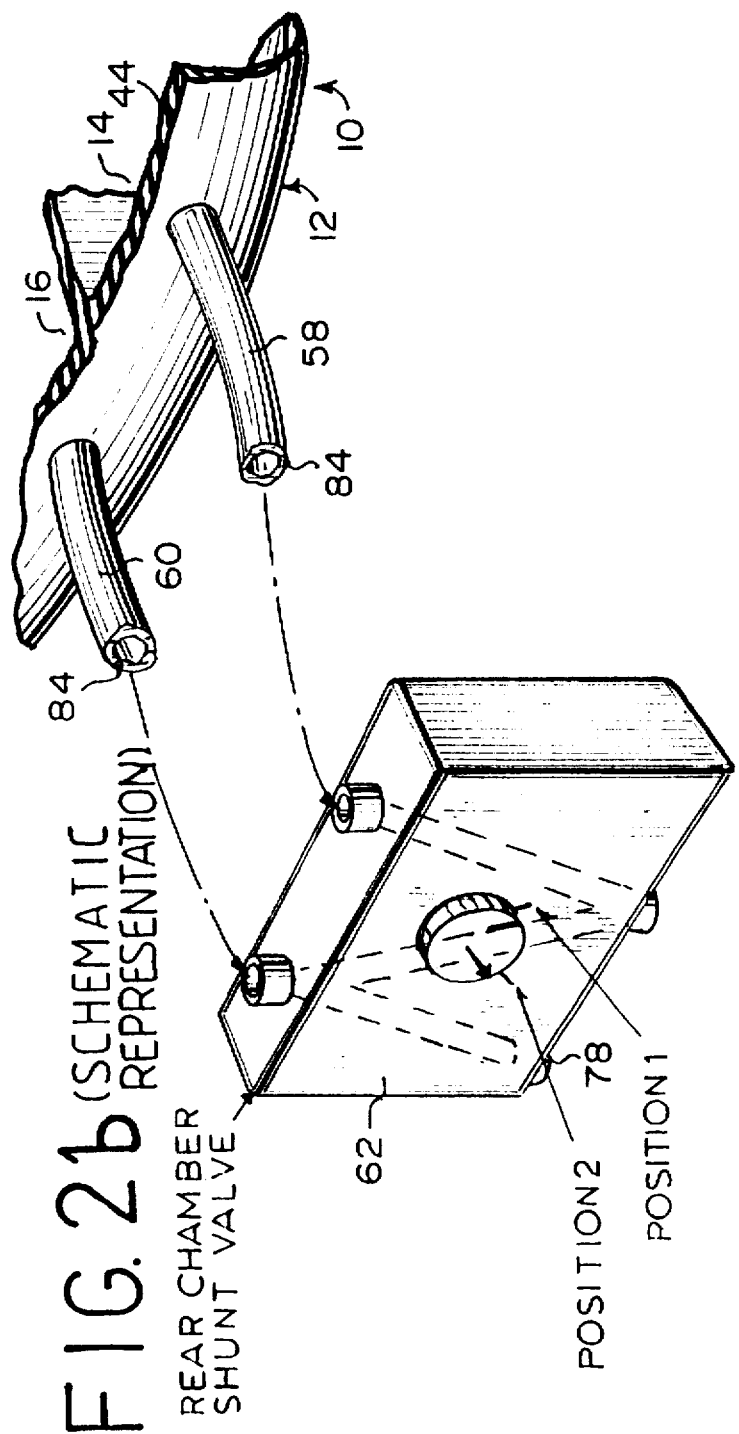

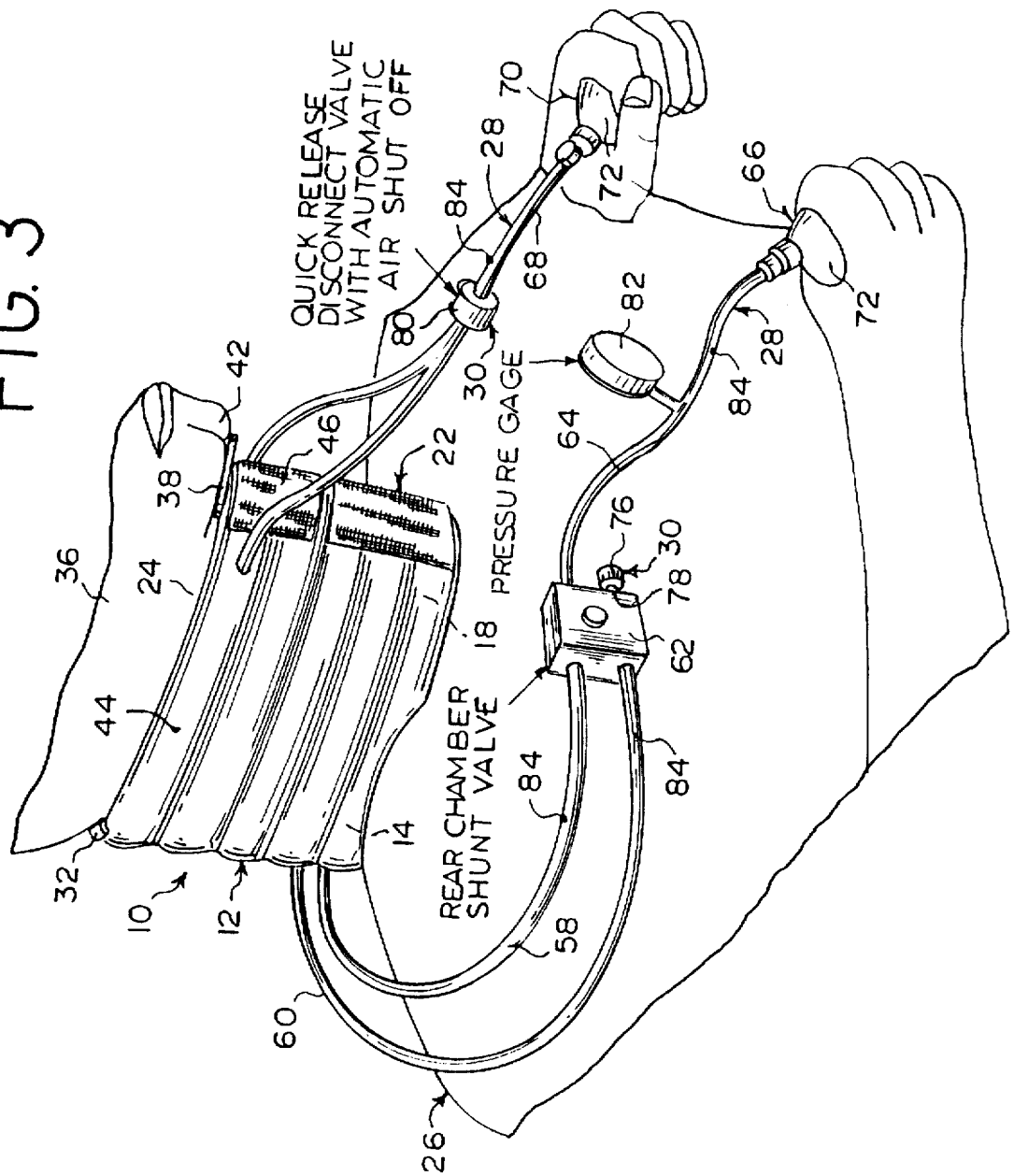

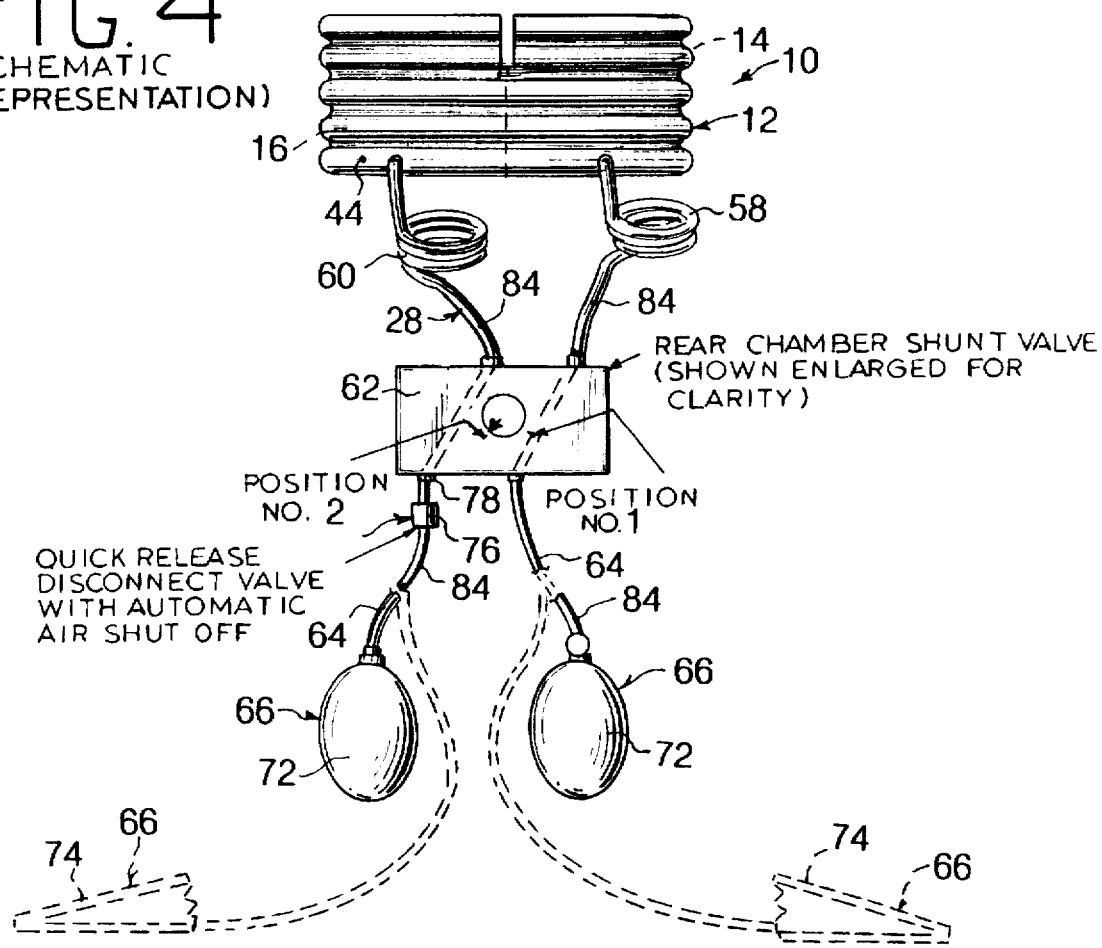

(OPTIONAL FOOT-OPERATED PUMPING STRUCTURE)

STEP 1
PLACING DEVICE AROUND THE NECK
FIGS. 1, 1a, 1b

- PLACE CERVICAL COLLAR AROUND THE NECK AND FASTEN WITH CLOSURE STRAPS
- PLACE MANDIBULAR (CHIN) CUP AT APPROPRIATE LOCATION AND FASTEN TO UPPER SURFACE OF CERVICAL COLLAR WITH FASTENING MEANS PROVIDED

STEP 2
INFLATING REAR CHAMBERS
FIGS. 2, 2a, 2b, 2c

- INFLATE REAR CHAMBER UNTIL UPPER SURFACE OF CERVICAL COLLAR TOUCHES THE BACK OF THE HEAD (OCCIPITAL)
- PLACE TWO OCCIPITAL CUPS UNDER THE EXTERNAL OCCIPITAL PROTUBERANCES AT THE BASE OF THE SKULL AND FASTEN TO THE UPPER SURFACE OF THE CERVICAL COLLAR WITH THE FASTENING MEANS PROVIDED

STEP 3
INFLATING FRONT CHAMBERS
FIG. 3

- INFLATE FRONT CHAMBER UNTIL THE THE MANDIBULAR CUP TOUCHES THE BOTTOM OF THE JAW
- CONTINUE INFLATING FRONT AND REAR CHAMBERS SIMULTANEOUSLY UNTIL DESIRED TRACTION FORCE IS ATTAINED AND MAKE NECESSARY ADJUSTMENTS IN FLEXION / EXTENSION (FORWARD / BACKWARD HEAD TILT) BY INCREASING THE PRESSURE IN THE CORRESPONDING POSTERIOR / ANTERIOR CHAMBERS

STEP 4
ADJUSTING SIDE TILT OF THE HEAD (LATERAL FLEXION)
FIGS. 4, 4a

- DISENGAGE PUMPING MEANS FROM FRONT CHAMBER CONNECT PUMPING MEANS TO FREE PORT OF SHUNTING VALVE AND SWITCH POSITION OF REAR CHAMBER SHUNTING VALVE SET LATERAL FLEXION OF THE HEAD BY ADJUSTING THE PRESSURE ON THE LEFT/ RIGHT SPLIT REAR CHAMBERS
- GRADUALLY RELEASE PRESSURE EVENLY FROM FRONT AND REAR CHAMBERS PRIOR TO REMOVAL OF COLLAR

FIG. 6

INFLATABLE CERVICAL TRACTION DEVICE

CROSS-REFERENCE TO RELATED APPLICATION

This application derives from and claims the benefit of U.S. Provisional Application No. 60/009,458, filed 29 Dec. 1995.

BACKGROUND OF THE INVENTION

1. Field of the Invention

The instant invention relates generally to cervical traction systems and more specifically it relates to a multichambered, inflatable cervical traction device.

The inflatable cervical traction device provides complete and precise control of the neck and head, so that it can be maintained in a neutral position during traction, to eliminate microtrauma and reactive muscle spasms that detract from the benefit of applying traction to the neck.

2. Description of the Prior Art

Numerous cervical traction systems have been provided in the prior art that are adapted to provide therapeutic supports for people having injured necks. While these units may be suitable for the particular purpose to which they address, they would not be as suitable for the purposes of the present invention as heretofore described.

SUMMARY OF THE INVENTION

The present invention is concerned with a multichambered, inflatable cervical traction device.

A first object of the present invention is to provide an inflatable cervical traction device that will overcome the shortcomings of the prior art devices.

A second object is to provide an inflatable cervical traction device that will allow infinite and independent control of the forward and backward tilt of the head (flexion/extension) to eliminate compression and irritation of the articular cartilage that lines the surface of the anterior and posterior cervical spine joints and of the temporomandibular (jaw) joints and eliminates pinching of the associated joint capsules.

Another object of the present invention is to provide an inflatable cervical traction device that will eliminate wedging of the cervical intervertebral discs.

Another object of the present invention is to provide an inflatable cervical traction device which will provide a safe and effective traction by eliminating further injury to the aforementioned structures and which will also prevent the onset of additional muscular spasms.

A further object of the present invention is to provide an inflatable cervical traction device that will allow infinite and independent control of the side tilt of the head (lateral flexion), and that will also eliminate compression and irritation of the cervical spine joints and wedging of cervical intervertebral discs for a safe and effective traction.

A still further object is to provide an inflatable cervical traction device that will allow infinite and precise control of the traction force for a safe and effective traction.

Yet another object of the present invention is to provide an inflatable cervical traction device that is easy to use while sitting, standing, reclining or walking, to allow greater freedom of activities while using the device and greater ease of use. This further allows the option of using the device while the muscular and skeletal structures associated with the spinal column are compensating to the gravitational field (person standing or sitting), or while these structures are decompensated to the gravitational field (person laying down and cervical structures of non-weight bearing orientation).

Another object is to provide an inflatable cervical traction device that is lightweight and compact to make it easy to carry when traveling.

A still further object is to provide an inflatable cervical traction device that is simple and easy to use.

Another object is to provide an inflatable cervical traction device that is economical in cost to manufacture.

The foregoing and other objects, advantages and characterizing features will become apparent from the following description of certain illustrative embodiments of the invention.

The novel features which are considered characteristic for the invention are set forth in the appended claims. The invention itself, however, both as to its construction and its method of operation, together with additional objects and advantages thereof, will be best understood from the following description of the specific embodiments when read and understood in connection with the accompanying drawings. Attention is called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views.

FIG. 2a is a rear elevational view taken in the direction of arrow 2a in FIG. 2 with parts broken away.

FIG. 2b is an enlarged perspective view showing the rear chamber shunt valve in greater detail.

FIG. 3 is a front perspective view similar to FIG. 2, showing the inflation of the front chambers.

FIG. 4 is a rear elevational view similar to FIG. 2c, showing the setting of the rear chamber shunt valve for side tilt adjustment of the head (lateral flexion).

FIG. 6 is a block diagram flow chart, showing the various steps of how to use the device.

Figure 1:
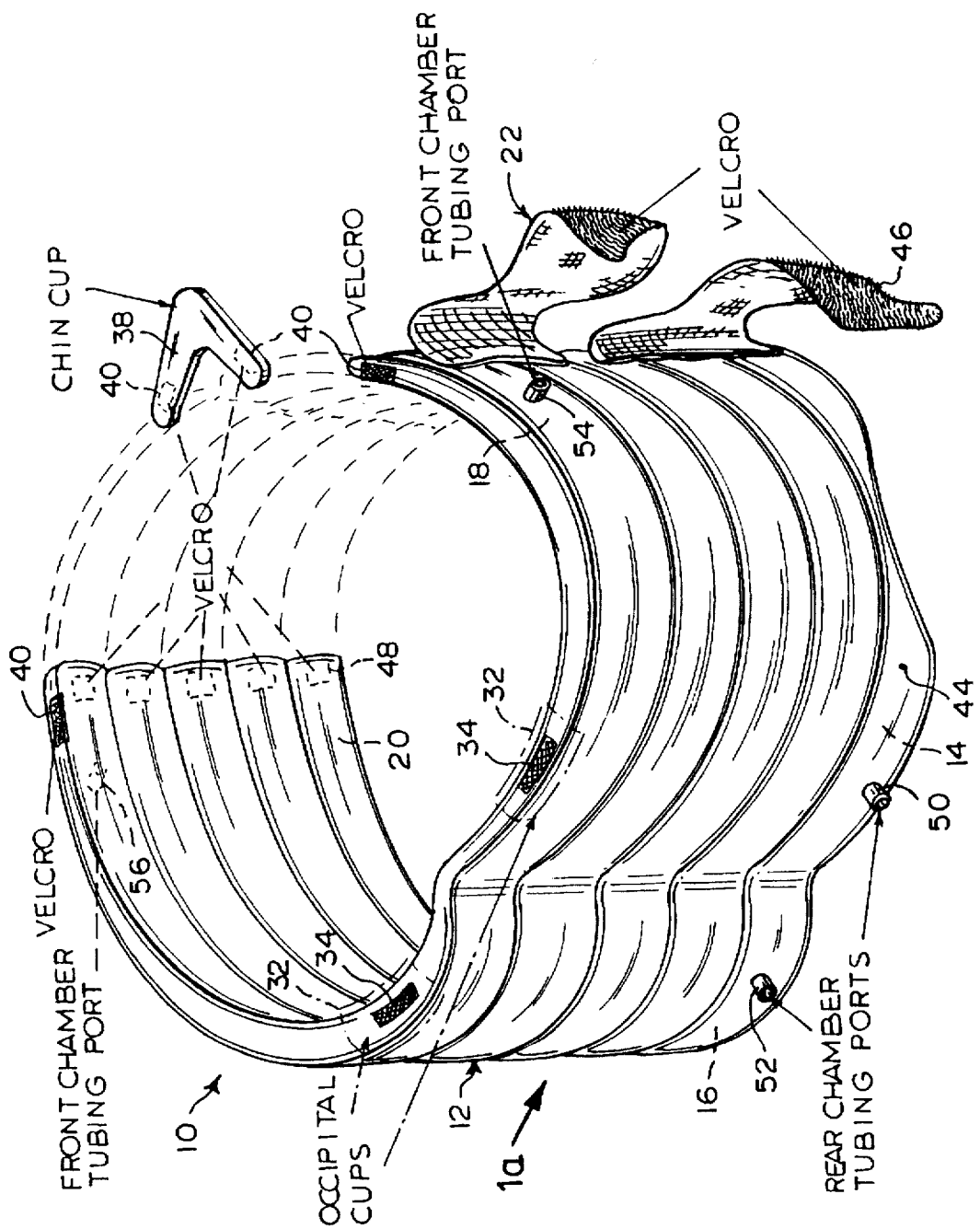
FIG. 1 is a rear perspective view of the device spread open.
Figure 1A:
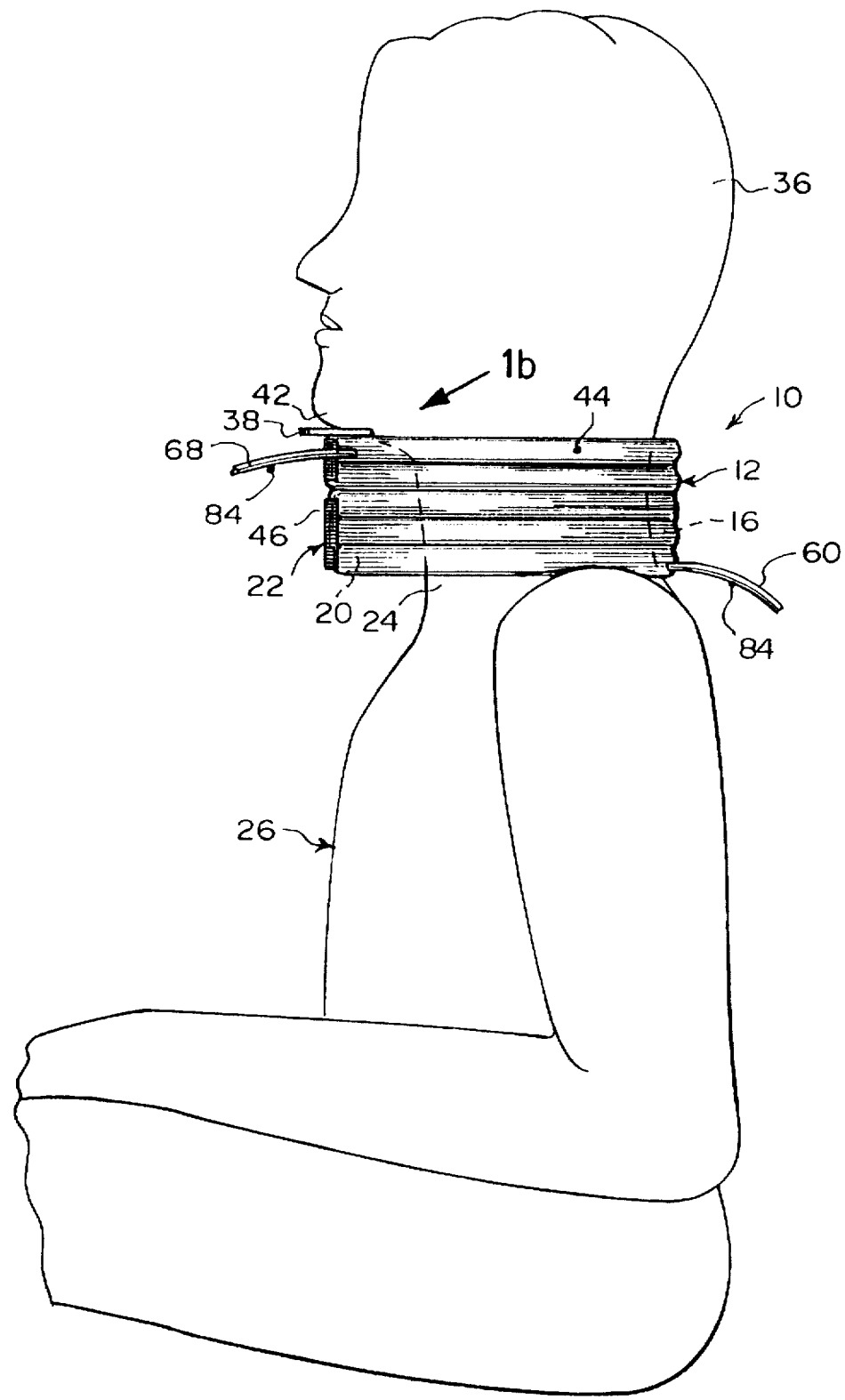
FIG. 1a is a side elevational view taken in the direction of arrow 1a in FIG. 1, with the device in place around a neck of a person.
Figure 1B:
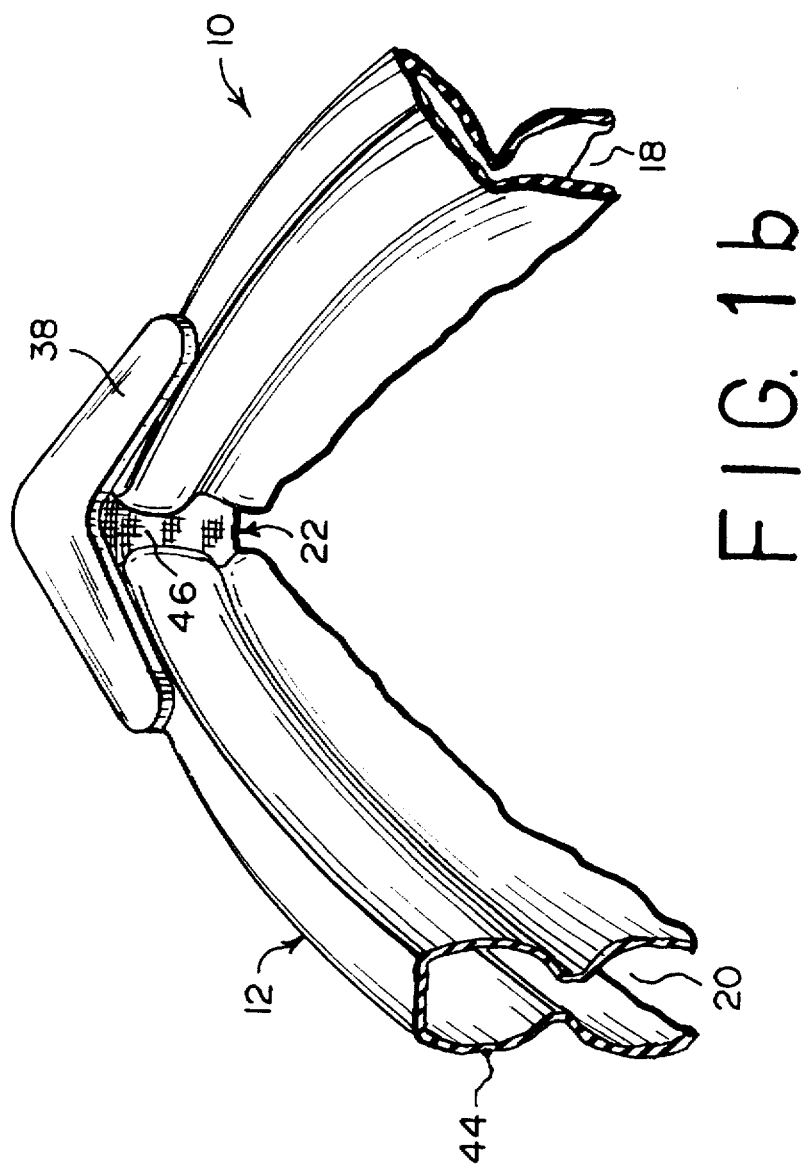
FIG. 1b is a partial enlarged perspective view taken in the direction of arrow 1b in FIG. 1a, showing the chin cup in greater detail.

List of Reference Numerals Used in the Drawing Figures 10 inflatable cervical traction device
12 C-shaped multi-ribbed inflatable hollow collar of 10
14 rear right chamber of 12
16 rear left chamber of 12
18 front right chamber of 12
20 front left chamber of 12
22 securing structure for 12
24 neck of 26
26 person
28 air pumping facility of 10
30 air releasing assembly of 10
32 occipital cup of 10
34 set of hook and look type fasteners for 32
36 head of 26
38 V-shaped mandibular cup of 10
40 set of hook and loop type fasteners for 38
42 chin of 26
44 flexible elastically expandable material of 12
46 hook and loop type fastener strap of 22
48 hook and loop type fastener tap of 22
50 rear right chamber tubing port of 28
52 rear left chamber tubing port of 28
54 front right chamber tubing port of 28
56 front left chamber tubing port of 28
58 first flexible tubing of 28 on 50
60 second flexible tubing of 28 on 52
62 two position rear chamber shunt valve of 28
64 third flexible tubing of 28 on 62
66 first air pump of 28 on 64
68 Y-shaped flexible tubing of 28 on 54 and 56
70 second air pump of 28 on 68
72 hand-held type for 66 and 70
74 foot-operated type of 66 and 70
76 first quick release disconnect valve with automatic air shut off of 30 on 78
78 free port on 62
80 second quick release disconnect valve with automatic air shut off of 30 on 78
82 pressure gauge on 64
84 material of 58, 60, 64 and 68

DETAILED DESCRIPTION OF THE PREFERRED EMBODIMENTS

Turning now descriptively to the drawings, in which similar reference characters denote similar elements throughout the several views, FIGS. 1 through 5 illustrate an inflatable cervical traction device 10 comprising a C-shaped multi-ribbed inflatable hollow collar 12, having four separate chambers 14, 16, 18 and 20. Two of the chambers 14 and 16 are located at rear right and left locations of the collar 12, while the other two chambers 18 and 20 are located at front right and left locations of the collar 12. Structures 22 are for securing two opposite front ends of the collar 12 together in a releasable manner, to hold the collar 12 about a neck 24 of a person 26.

A facility 28 is for pumping air into the four chambers 14, 16, 18 and 20 of the collar 12 to inflate each of the four chambers 14, 16, 18 and 20 at various pressurized amounts, so that the collar 12 can properly and adjustably support the neck 24 of the person 26. An assembly 30 is for releasing air from the four chambers 14, 16, 18 and 20 of the collar 12, so that the collar 12 can deflate to be easily removed from the neck 24 of the person 26.

A pair of occipital cups 32 are provided. Two sets of hook and loop type fasteners (for example, VELCRO®) 34 are for securing the occipital cups 32 in spaced apart positions onto a top rear edge of the collar 12 in a releasable manner, for increased positive contacts with the back of the head 36 of the person 26.

A V-shaped mandibular cup 38 is also provided. Two sets of hook and loop type fasteners 40 are for securing the mandibular cup 38 onto two top front edges of the collar 12 in a releasable manner for an increased positive contact with the chin 42 of the person 26.

The collar 12 is fabricated out of a flexible elastically expandable material 44. The flexible elastically expandable material 44 is selected from the group consisting of plastic, such as polyethylene, rubber and/or similar natural and synthetic substances.

The securing structure 22 includes at least one hook and loop type fastener strap 46 affixed at one end to one front end of the collar 12. At least one hook and loop type fastener tab 48 is affixed onto other front end of the collar 12, so that the at least one hook and loop type fastener strap 46 can mate with the at least one hook and loop type fastener tab 48.

The air pumping facility 28 consists of four tubing ports 50, 52, 54 and 56, in which each tubing port is located on the collar 12 at one of the chambers. Two flexible tubings 58 and 60 extend from the two rear chamber tubing ports 50 and 52. A two position rear chamber shunt valve 62 is connected to the two flexible tubings 58 and 60. A third flexible tubing 64 extends from the rear chamber shunt valve 62. A first air pump 66 is connected to the third flexible tubing 64. A Y-shaped flexible tubing 68 extends from the two front chamber tubing ports 54 and 56. A second air pump 70 is connected to the Y-shaped flexible tubing 68.

The first air pump 66 and the second air pump 70 can be hand-held types 72. The first air pump 66 and the second air pump 70 can also be foot-operated types 74.

The air releasing assembly 30 comprises a first quick release disconnect valve with an automatic air shut off 76 connected to a free port 78 on the rear chamber shunt valve 62. A second quick release disconnect valve with an automatic air shut off 80 is in the Y-shaped flexible tubing 68.

Figure 2:
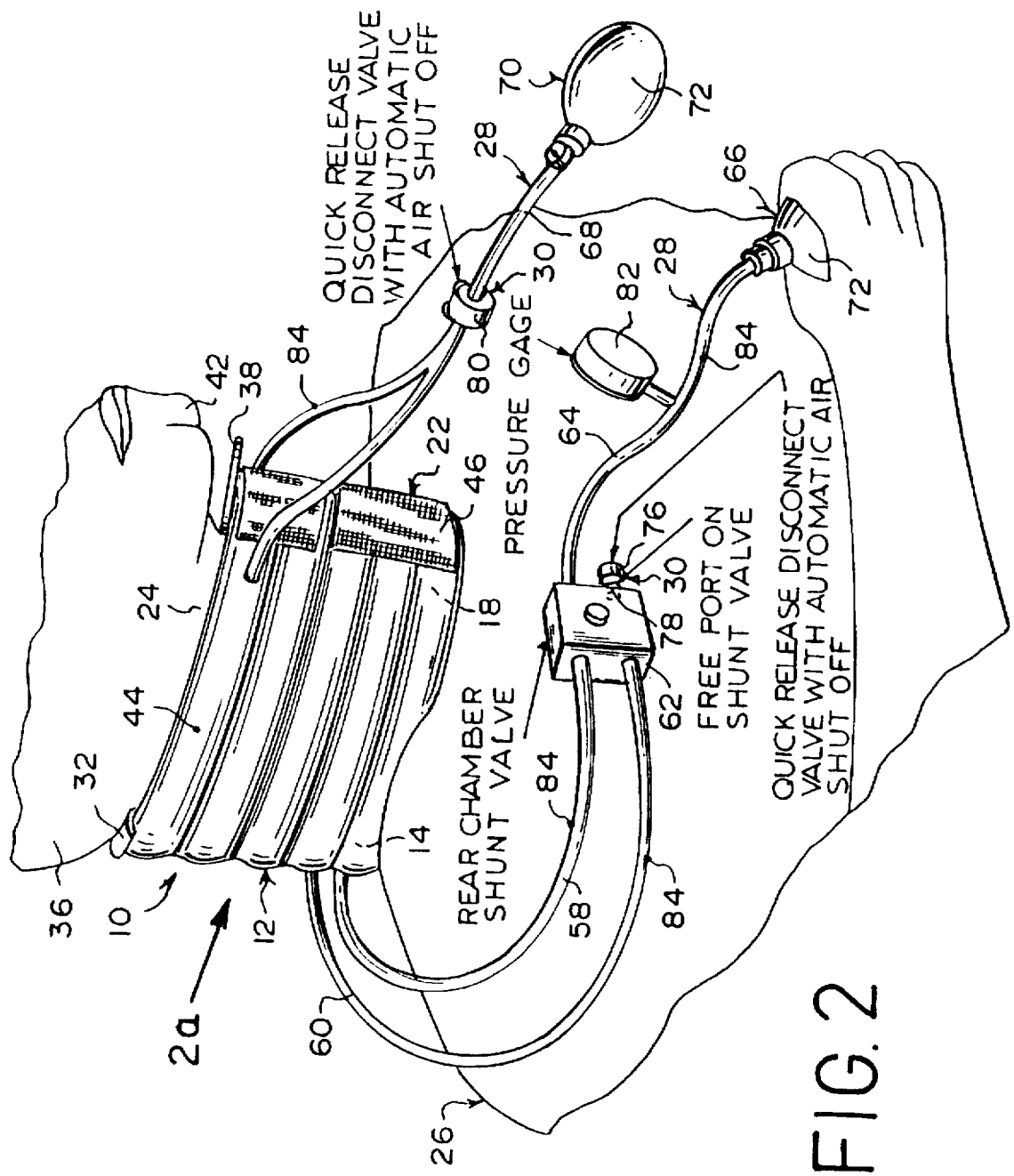
FIG. 2 is a front perspective view showing the inflation of the rear chambers.
Figure 2C:
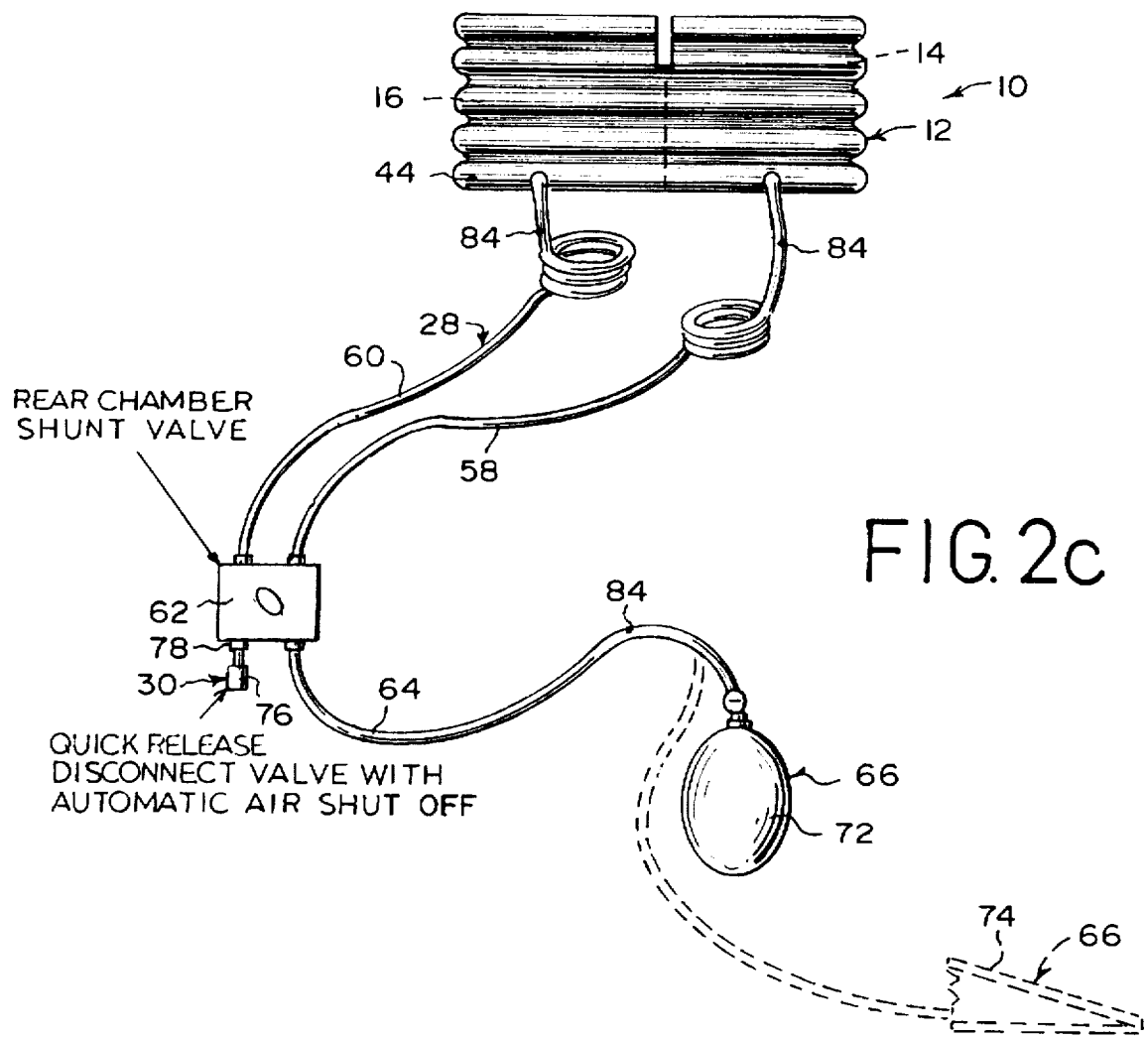
FIG. 2c is a rear elevational view showing the inflating of the rear chambers and the setting of the rear chamber shunt valve.
Figure 4A:
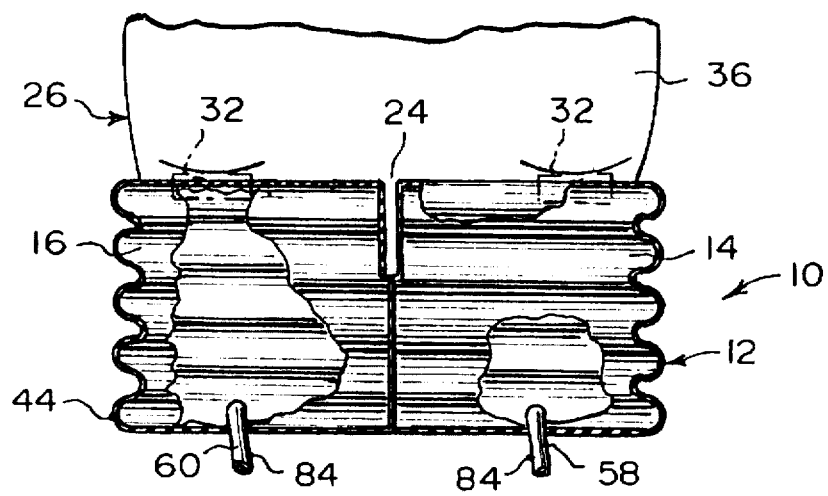
FIG. 4a is a rear elevational view similar to FIG. 2a with parts broken away and in section.
Figure 5:
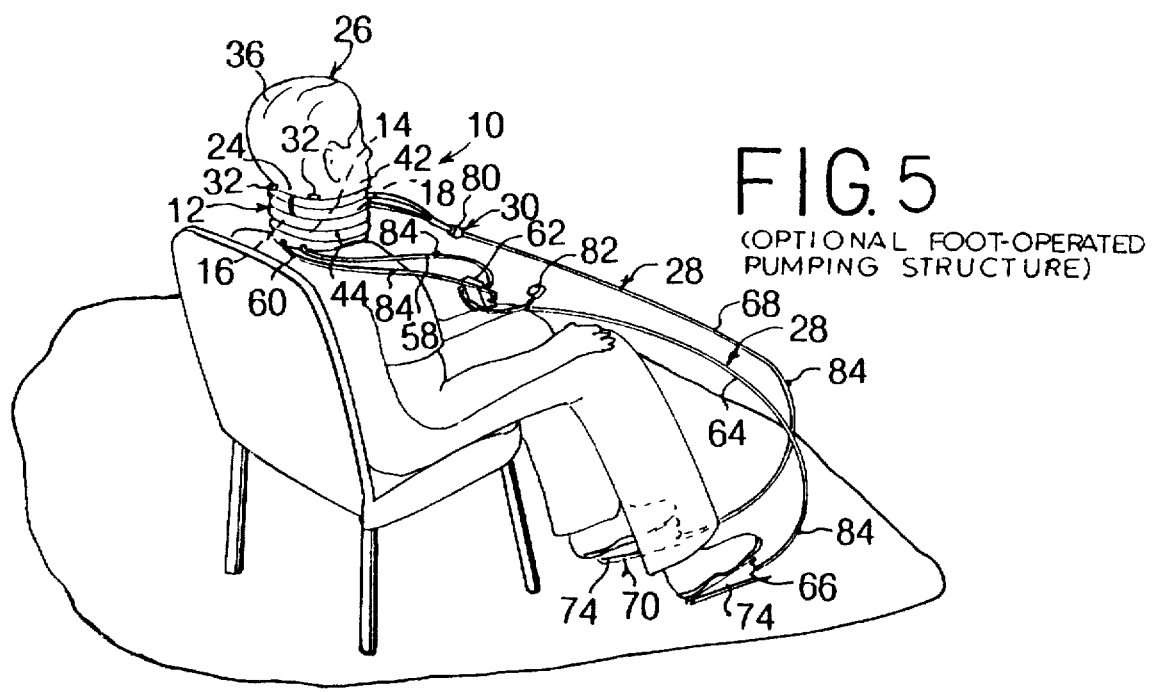
FIG. 5 is a rear perspective view of a person wearing the device, sitting in a chair and operating foot-operated pumping structures.

A pressure gauge 82, as shown in FIGS. 2, 3 and 5, can be mounted to the third flexible tubing 64 to facilitate reproducible settings in the course of a therapeutic process. The three flexible tubings 58, 60 and 64 and the Y-shaped flexible tubing 68 are fabricated out of a material 84 selected from the group consisting of plastic, rubber and similar natural and/or synthetic substances.

FIG. 6 is a block diagram flow chart for the instant invention. It outlines the various steps and sub-steps needed to be followed to use the inflatable cervical traction device 10 in the proper manner.

Another preferred embodiment of the invention concerns an inflatable cervical traction device having a plurality of interconnected, vertically-stacked, C-shaped, inflatable chambers wherein, when said device is placed around the neck of a person, each said chamber extends substantially around the neck of the person; a plurality of first partitions disposed within at least one of the chambers such that this partitioned chamber contains separately inflatable front and rear portions; means for separately inflating the front and rear portions; means for separately deflating the front and rear portions; and means for securing the device releasably around the neck of the person.

In its preferred embodiment, the device further contains a plurality of second partitions disposed within at least one of the chambers such that this second partitioned chamber contains separately inflatable left and right rear portions, including means for separately inflating and deflating the left and right portions. In another preferred embodiment, when worn about the neck of a person, the ends of each C-shaped chamber overlap opposite ends of vertically adjacent C-shaped chambers at the back of the neck of the wearer. In this alignment, the securing means is preferably hook and loop type fasteners disposed on the overlapping ends of the C-shaped chambers.

The device of the present invention will generally contain from 3 to 7 of the vertically-stacked, C-shaped chambers, preferably from 4 to 6.

With regard to the inflating means, the preferred means includes at least two tubing ports, a front tubing port located on the front portion of a partitioned chamber, and a rear tubing port located on the rear portion of a partitioned chamber; a flexible tubing releasably connected to each said tubing port; and an air pump connected to a distal end of each said flexible tubing. When the device is further partitioned into three or more separately inflatable portions, each said portion requires a tubing port. Because the individual, vertically-stacked C-shaped chambers are interconnected, it can readily be appreciated that the device can function adequately with as few as two tubing ports, for front and rear portions, or three tubing ports, when the rear portion is further partitioned into right and left portions.

The particular choice of inflating means is not critical, but will preferably include, for each separately inflatable portion, a tubing port located on that portion of a partitioned chamber, a flexible tubing releasably connected to each such tubing port, and an air pump connected to a distal end of each such flexible tubing. The air pump can be a hand-held, manually-operated air pump, such as, for example, a sphygmomanometer-type bulb, or can be a foot-operated air pump or a powered pump.

For releasing the air in the inflated device, for example, when removing the device, the chambers are deflated, for example, via a quick-release open/close valve integral with each port.

While the invention has been illustrated and described as embodied in a multichambered, inflatable cervical traction device, it is not intended to be limited to the details shown, since it will be understood that various omissions, modifications, substitutions and changes in the forms and details of the formulation illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of this invention.

What is claimed as new and desired to be protected by Letters Patent is set forth in the appended claims.

I claim:

1. An inflatable cervical traction device comprising:
   a) a C-shaped multi-ribbed inflatable hollow collar having four separate chambers, in which two of said chambers are located at rear right and left locations of said collar, while other two of said chambers are located at front right and left locations of said collar;
   b) means for securing two opposite front ends of said collar together in a releasable manner to hold said collar about a neck of a person;
   c) means for pumping air into said four chambers of said collar, to inflate each of said four chambers at various pressurized amounts, so that said collar can properly support the neck of the person;
   d) means for releasing air from said four chambers of said collar, so that said collar can deflate to be easily removed from the neck of the person;
   e) a V-shaped mandibular cup; and
   f) two sets of hook and loop fasteners for securing said mandibular cup onto two top front edges of said collar in a releasable manner for an increased positive contact with the chin of the person.

2. An inflatable cervical traction device as recited in claim 1, wherein said collar is fabricated out of a flexible elastically expandable material.

3. An inflatable cervical traction device as recited in claim 2, wherein said flexible elastically expandable material is selected from plastic and rubber.

4. An inflatable cervical traction device as recited in claim 1, wherein said securing means includes:
   a) at least one hook and loop fastener strap affixed at one end to one said front end of said collar; and
   b) at least one hook and loop fastener tab affixed onto other said front end of said collar, so that said at least one hook and loop fastener strap can mate with said at least one hook and loop fastener tab.

5. An inflatable cervical traction device as recited in claim 1, wherein said air pumping means includes:
   a) four tubing ports, in which each said tubing port is located on said collar at one of said chambers;
   b) two flexible tubings extending from said two rear chamber tubing ports;
   c) a two position rear chamber shunt valve connected to said two flexible tubings;
   d) a third flexible tubing extending from said rear chamber shunt valve;
   e) a first air pump connected to said third flexible tubing;
   f) a Y-shaped flexible tubing extending from said two front chamber tubing ports; and
   g) a second air pump connected to said Y-shaped flexible tubing.

6. An inflatable cervical traction device as recited in claim 5, wherein said first air pump and said second air pump are hand-held.

7. An inflatable cervical traction device as recited in claim 5, wherein said first air pump and said second air pump are foot-operated.

8. An inflatable cervical traction device as recited in claim 5, further including a pressure gauge mounted to said third flexible tubing to facilitate reproducible settings in the course of a therapeutic process.

9. An inflatable cervical traction device as recited in claim 5, wherein said three flexible tubing and said Y-shaped flexible tubing are fabricated out of a material selected from plastic and rubber.

10. An inflatable cervical traction device as recited in claim 1, wherein said air releasing means includes:
    a) a first quick release disconnect valve with automatic air shut off connected to a free port on said rear chamber shunt valve; and
    b) a second quick release disconnect valve with automatic air shut off in said Y-shaped flexible tubing.

11. An inflatable cervical traction device comprising:
    a) a C-shaped multi-ribbed inflatable hollow collar having four separate chambers, in which two of said chambers are located at rear right and left locations of said collar, while other two of said chambers are located at front right and left locations of said collar;

b) means for securing two opposite front ends of said collar together in a releasable manner to hold said collar about a neck of a person;

c) means for pumping air into said four chambers of said collar, to inflate each of said four chambers at various pressurized amounts, so that said collar can properly support the neck of the person;

d) means for releasing air from said four chambers of said collar, so that said collar can deflate to be easily removed from the neck of the person;

e) a pair of occipital cups; and f) two sets of hook and loop fasteners for securing said occipital cups in spaced apart positions onto a top rear edge of said collar in a releasable manner for increased positive contacts with the back of the head of the person.

12. An inflatable cervical traction device comprising:

a) a C-shaped multi-ribbed inflatable hollow collar having four separate chambers, in which two of said chambers are located at rear right and left locations of said collar, while other two of said chambers are located at front right and left locations of said collar;

b) means for securing two opposite front ends of said collar together in a releasable manner to hold said collar about a neck of a person;

c) means for pumping air into said four chambers of said collar, to inflate each of said four chambers at various pressurized amounts, so that said collar can properly support the neck of the person;

d) means for releasing air from said four chambers of said collar, so that said collar can deflate to be easily removed from the neck of the person;

e) a pair of occipital cups;

f) two sets of hook and loop fasteners for securing said occipital cups in spaced apart positions onto a top rear edge of said collar in a releasable manner for increased positive contacts with the back of the head of the person;

g) a V-shaped mandibular cup; and h) two sets of hook and loop type fasteners for securing said mandibular cup onto two top front edges of said collar in a releasable manner for an increased positive contact with the chin of the person.

13. An inflatable cervical traction device as recited in claim 12, wherein said collar is fabricated out of a flexible elastically expandable material.

14. An inflatable cervical traction device as recited in claim 13, wherein said flexible elastically expandable material is selected from plastic and rubber.

15. An inflatable cervical traction device as recited in claim 14, wherein said securing means includes:

a) at least one hook and loop fastener strap affixed at one end to one said front end of said collar; and b) at least one hook and loop fastener tab affixed onto other said front end of said collar, so that said at least one hook and loop fastener strap can mate with said at least one hook and loop type fastener tab.

16. An inflatable cervical traction device as recited in claim 15, wherein said air pumping means includes:

a) four tubing ports, in which each said tubing port is located on said collar at one of said chambers;

b) two flexible tubings extending from said two rear chamber tubing ports;

c) a two position rear chamber shunt valve connected to said two flexible tubings;

d) a third flexible tubing extending from said rear chamber shunt valve;

e) a first air pump connected to said third flexible tubing;

f) a Y-shaped flexible tubing extending from said two front chamber tubing ports; and g) a second air pump connected to said Y-shaped flexible tubing.

17. An inflatable cervical traction device as recited in claim 16, wherein said first air pump and said second air pump are hand-held.

18. An inflatable cervical traction device as recited in claim 16, wherein said first air pump and said second air pump are foot-operated.

19. An inflatable cervical traction device as recited in claim 16, wherein said air releasing means includes:

a) a first quick release disconnect valve with automatic air shut off connected to a free port on said rear chamber shunt valve; and b) a second quick release disconnect valve with automatic air shut off in said Y-shaped flexible tubing.

20. An inflatable cervical traction device as recited in claim 19, further including a pressure gauge mounted to said third flexible tubing to facilitate reproducible settings in the course of a therapeutic process.

21. An inflatable cervical traction device as recited in claim 20, wherein said three flexible tubing and said Y-shaped flexible tubing are fabricated out of a material selected from the group consisting of plastic, rubber and similar natural/synthetic substances.

* * * * *